United States Patent
Bell et al.

(10) Patent No.: US 9,452,982 B2
(45) Date of Patent: Sep. 27, 2016

(54) PYRIDINYL CYCLOHEXANECARBOXAMIDE COOLING COMPOUNDS

(75) Inventors: Karen Ann Bell, Loveland, OH (US); Christophe C. Galopin, Chesterfield, VA (US); Jay Patrick Slack, Loveland, OH (US); Lori W. Tigani, Salisbury, MD (US)

(73) Assignee: Givaudan, S.A., Vernier (CH)

( * ) Notice: Subject to any disclaimer, the term of this patent is extended or adjusted under 35 U.S.C. 154(b) by 1484 days.

(21) Appl. No.: 11/990,103

(22) PCT Filed: Aug. 14, 2006

(86) PCT No.: PCT/CH2006/000427
§ 371 (c)(1),
(2), (4) Date: Sep. 16, 2009

(87) PCT Pub. No.: WO2007/019719
PCT Pub. Date: Feb. 22, 2007

(65) Prior Publication Data
US 2010/0035938 A1    Feb. 11, 2010

Related U.S. Application Data

(60) Provisional application No. 60/708,153, filed on Aug. 15, 2005.

(51) Int. Cl.
| | | |
|---|---|---|
| A61K 31/44 | (2006.01) | |
| C07D 213/40 | (2006.01) | |
| A23L 2/56 | (2006.01) | |
| A61K 8/49 | (2006.01) | |
| A61Q 11/00 | (2006.01) | |

(52) U.S. Cl.
CPC ............... *C07D 213/40* (2013.01); *A23L 2/56* (2013.01); *A61K 8/4926* (2013.01); *A61Q 11/00* (2013.01); *A61K 2800/244* (2013.01)

(58) Field of Classification Search
CPC ............ A23L 2/56; A23L 2/00; A23L 2/52; A61K 2800/244; A61K 8/4926; A61K 8/00; A61K 8/18; A61K 8/19; A61K 8/46; A61K 8/4906; A61K 2800/00; A61K 2800/20; A61K 2800/24; C07D 213/40; C07D 213/00; C07D 213/02; C07D 213/04; C07D 213/24; C07D 213/36; A61Q 11/00
USPC ............ 426/533, 531, 536, 537; 546/1, 314, 546/323, 334, 336; 514/183, 277, 354, 357
See application file for complete search history.

(56) References Cited

U.S. PATENT DOCUMENTS

| | | |
|---|---|---|
| 3,516,943 A | 6/1970 | Brynko et al. |
| 4,136,163 A * | 1/1979 | Watson et al. .................. 424/54 |
| 4,150,052 A | 4/1979 | Watson et al. |
| 4,190,643 A | 2/1980 | Rowsell et al. |
| 4,285,984 A | 8/1981 | Huber |
| 5,759,599 A | 6/1998 | Wampler et al. |
| 6,039,901 A | 3/2000 | Soper et al. |
| 6,045,835 A | 4/2000 | Soper et al. |
| 6,056,949 A | 5/2000 | Menzi et al. |
| 6,106,875 A | 8/2000 | Soper et al. |
| 6,123,974 A | 9/2000 | Gautschi et al. |
| 6,222,062 B1 | 4/2001 | Anderson et al. |
| 6,306,818 B1 | 10/2001 | Anderson et al. |
| 6,325,859 B1 | 12/2001 | De Roos et al. |
| 6,325,951 B1 | 12/2001 | Soper et al. |

(Continued)

FOREIGN PATENT DOCUMENTS

| | | |
|---|---|---|
| AU | 75931/74 | 3/1976 |
| CH | 491 111 A | 5/1970 |
| DE | 24 58 562 A1 | 6/1975 |
| GB | 1 351 761 A | 5/1974 |
| WO | WO 93/23005 A | 11/1993 |
| WO | WO 01/03825 A | 1/2001 |
| WO | WO 2004/034791 A | 4/2004 |
| WO | WO 2005/002582 A | 1/2005 |
| WO | WO 2005/020897 A | 3/2005 |
| WO | WO 2006/056087 A1 | 6/2006 |
| WO | WO 2006/056096 A | 6/2006 |
| WO | WO 2006/092076 A | 9/2006 |

*Primary Examiner* — Nikki H Dees
(74) *Attorney, Agent, or Firm* — Curatolo Sidoti Co., LPA; Joseph G. Curatolo; Salvatore A. Sidoti

(57) ABSTRACT

A method of providing a cooling effect to a product includes the incorporation into the product of at least one compound of the formula I

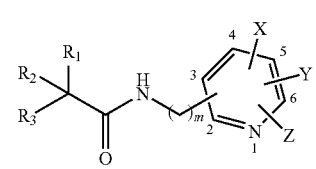

in which m is a number between 0 and 2, X, Y and Z are selected independently from the group consisting of H, halogen, OH, Me, Et, MeO and EtO, and $R^1$, $R^2$ and $R^3$ together comprise at least 6 carbons, selected such that (a) (i) $R^1$ is selected from the group consisting of H, Me, Et, isopropyl and $C_4$-$C_5$ branched alkyl; and (ii) $R^2$ and $R^3$ are independently selected from the group consisting of Me, Et, isopropyl and $C_4$-branched alkyl; or (b) any two or all of $R^1$, $R^2$ and $R^3$ together form a monocyclic, bicyclic or tricyclic radical having up to 10 carbons.

The compounds confer substantial cooling effects on compositions applied to the skin or taken orally, such as toothpastes, mouthwashes, foodstuffs, beverages, confectionery, tobacco products, skin creams and ointments.

24 Claims, No Drawings

(56) References Cited

U.S. PATENT DOCUMENTS

| | | |
|---|---|---|
| 6,335,047 B1 | 1/2002 | Daniher et al. |
| 6,348,618 B1 | 2/2002 | Anderson et al. |
| 6,348,625 B1 | 2/2002 | Anderson et al. |
| 6,387,431 B1 | 5/2002 | Gautschi |
| 6,426,108 B1 | 7/2002 | Gautschi |
| 6,436,461 B1 | 8/2002 | Bouwmeesters et al. |
| 6,440,912 B2 | 8/2002 | McGee et al. |
| 6,451,366 B1 | 9/2002 | Daniher et al. |
| 6,482,433 B1 | 11/2002 | De Roos et al. |
| 6,610,346 B1 | 8/2003 | Acuna et al. |
| 6,689,740 B1 | 2/2004 | McGee et al. |
| 6,805,893 B2 | 10/2004 | Acuna et al. |
| 6,869,923 B1 | 3/2005 | Cunningham et al. |
| 2001/0008635 A1 | 7/2001 | Quellet et al. |
| 2002/0081370 A1 | 6/2002 | Daniher et al. |
| 2003/0082272 A1 | 5/2003 | Bouwmeesters et al. |
| 2003/0165587 A1 | 9/2003 | Binggeli et al. |
| 2004/0047960 A1 | 3/2004 | Acuna et al. |
| 2005/0054651 A1* | 3/2005 | Natarajan et al. ............ 514/249 |
| 2005/0187211 A1* | 8/2005 | Wei ............................ 514/223.8 |
| 2005/0214337 A1 | 9/2005 | McGee et al. |
| 2005/0227906 A1 | 10/2005 | Schudel et al. |
| 2005/0233042 A1 | 10/2005 | Galopin et al. |
| 2006/0035008 A1 | 2/2006 | Virgallito et al. |
| 2006/0051301 A1 | 3/2006 | Galopin et al. |
| 2006/0154850 A1 | 7/2006 | Quellet et al. |
| 2006/0172917 A1 | 8/2006 | Vedantam et al. |
| 2006/0276667 A1 | 12/2006 | Galopin et al. |
| 2008/0319055 A1 | 12/2008 | Cole et al. |

* cited by examiner

PYRIDINYL CYCLOHEXANECARBOXAMIDE COOLING COMPOUNDS

CROSS REFERENCE TO RELATED APPLICATIONS

This application is a national stage application of International Application No. PCT/CH2006/000427, filed Aug. 14, 2006, which claims the benefit of U.S. Provisional Patent Application No. 60/708,153, filed Aug. 15, 2005, from which applications priority is claimed, and which are incorporated herein by reference.

This invention relates to cooling compounds.

Cooling compounds, that is, chemical compounds that impart a cooling sensation to the skin or the mucous membranes of the body, are well known to the art and are widely used in a variety of products such as foodstuffs, tobacco products, beverages, dentifrices, mouthwashes and toiletries.

One class of cooling compounds that have enjoyed substantial success consists of N-substituted p-menthane carboxamides. Examples of these compounds are described in, for example, British Patents GB 1,351,761-2 and U.S. Pat. No. 4,150,052.

It has now been found that a particular selection of such compounds exhibits a cooling effect that is both surprisingly strong and long-lasting. A method is provided, therefore, of providing a cooling effect to a product, comprising the incorporation into the product of at least one compound of the formula I

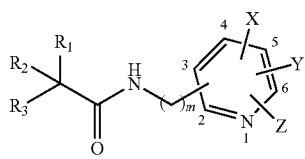

I in which m is a number between 0 and 2, X, Y and Z are selected independently from the group consisting of H, halogen, OH, Me, Et, MeO and EtO, and $R^1$, $R^2$ and $R^3$ together comprise at least 6 carbons, selected such that
(a) (i) $R^1$ is selected from the group consisting of H, Me, Et, isopropyl and $C_4$-$C_5$ branched alkyl; and
(ii) $R^2$ and $R^3$ are independently selected from the group consisting of Me, Et, isopropyl and $C_4$-branched alkyl; or
(b) any two or all of $R^1$, $R^2$ and $R^3$ together form a monocyclic, bicyclic or tricyclic radical having up to 10 carbons.

Me is defined as methyl, and Et is defined as ethyl.

Examples of cyclic radicals as described under (b) above include 3-para-menthyl, bornyl and adamantyl.

The compounds of formula (I) may comprise one or more chiral centres and as such may exist as a mixture of stereoisomers, or they may be resolved as isomerically pure forms. Resolving stereoisomers adds to the complexity of manufacture and purification of these compounds and so it is preferred to use the compounds as mixtures of their stereoisomers simply for economic reasons. However, if it is desired to prepare individual stereoisomers, this may be achieved according to methods known in the art, e.g. preparative HPLC and GC or by stereoselective syntheses.

In some embodiments, the compounds are those in which X, Y, Z are H, OH, Me or OMe. In certain embodiments, the compounds are those in which m is 2; X, Y and Z are H or Me and $R^1$, $R^2$ and $R^3$ are taken from Table 1.

TABLE 1

Exemplary $R^1$, $R^2$ and $R^3$ groups.

| $R^1$ | $R^2$ | $R^3$ |
|---|---|---|
| H | | bornyl |
| H | | 3-p-menthyl |
| H | isopropyl | isopropyl |
| methyl | isopropyl | isopropyl |
| ethyl | ethyl | ethyl |
| | adamantyl | |

A particularly effective compound is that in which $R^1$ is H and $R^2$ and $R^3$ together form a 3-p-menthyl ring.

Examples of effective compounds are (1R,2S,5R)-2-isopropyl-5-methyl-N-(pyridinalkyl)cyclohexanecarboxamide and (2S,5R)-2-isopropyl-5-methyl-N-(pyridinalkyl)cyclohexanecarboxamide. Particular examples of these are (1R,2S,5R)-2-isopropyl-5-methyl-N-(2-(pyridin-4-yl)ethyl)cyclohexanecarboxamide and (2S,5R)-2-isopropyl-5-methyl-N-(2-(pyridin-4-yl)ethyl)cyclohexanecarboxamide Certain of the compounds are novel. A compound is therefore provided of the formula I as hereinabove described, in which m=2 and X, Y, Z, $R^1$, $R^2$, $R^3$ have the meanings given hereinabove, with the proviso that when $R^2$ and $R^3$ form a para-menthyl ring, at least one of $R^1$, X, Y and Z is a moiety other than H.

A compound is also provided according to formula I as hereinabove described, in which X, Y, Z, $R^1$ are H and $R^2$, $R^3$ have the meanings given hereinabove.

In certain embodiments $R^1$ is hydrogen and $R^2$ and $R^3$ are independently selected from the group consisting of Me, Et and $C_3$-$C_4$ branched alkyl; or $R^1$, $R^2$ and $R^3$ together form a monocyclic, bicyclic or tricyclic radical having up to 10 carbons.

The compounds may be easily prepared and isolated by art-recognized methods

They are distinguished from similar compounds of the prior art by their surprisingly high cooling effect (up to 100 times higher than that of similar known compounds) and by the longevity of the cooling effect. These compounds also have a high solubility in oily solvents, such as mint oils, and acidic aqueous solutions, such as soft drinks. These features expand the uses of cooling compounds to a larger variety of products The compounds may be used in products that are applied to the mouth or the skin to give a cooling sensation. By "applying" is meant any form of bringing into contact, for example, oral ingestion or, in the case of tobacco products, inhalation. In the case of application to the skin, it may be, for example, by including the compound in a cream or salve, or in a sprayable composition. There is also provided, therefore, a method of providing a cooling effect to the mouth or skin by applying thereto a product comprising a compound as hereinabove described.

The range of products in which the compounds may be used is very wide, and it includes by way of example only, dentifrices such as toothpaste and toothgel, mouthwashes, foodstuffs, beverages, confectionery, tobacco products, skin creams and ointments, both cosmetic and medicinal.

The compounds may be used alone or in combination with other cooling compounds known in the art, e.g., menthol, menthone, isopulegol, N-ethyl p-menthanecarboxamide (WS-3), N,2,3-trimethyl-2-isopropylbutanamide (WS-23), menthyl lactate (Frescolat™ ML), menthone glycerine acetal (Frescolat™ MGA), mono-menthyl succinate (Physcool™), mono-menthyl glutarate, O-menthyl glycerine (CoolAct™ 10), menthyl-N,N-dimethylsuccinamate and 2-sec-butylcyclohexanone (Freskomenthe™).

Certain embodiments are now further described by means of the following non-limiting examples.

EXAMPLE 1

Preparation of N-(4-pyridinyl) p-menthanecarboxamide

To a flask are added 4.7 g (50 mmol) of pyridin-4-ylamine, 4.04 mL of pyridine and 100 mL MtBE. To this mixture, 10 g of p-menthanecarboxyl chloride are added dropwise over 5 minutes. The reaction mixture is stirred for 24 hours. To the reaction mixture, 50 mL of water are added. The mixture is separated. The organic layer is washed with 50 mL of water and 50 mL of brine. The organic layer is dried over $MgSO_4$. The solvent is evaporated in vacuo to afford the crude product, which is recrystallized from hexanes to afford 6.2 g of the desired product with the following spectroscopic properties:

MS: 260 ([M$^{+\bullet}$]), 217, 149, 121, 95
$^1$H NMR (300 MHz; CDCl$_3$) δ: 8.49 (d, 2H), 7.77 (s, 1H), 7.52 (d, 2H), 2.22 (td, 1H), 1.9 (broad d, 2H), 1.85-1.57 (m, 3H), 1.44-1.22 (m, 2H), 1.16-0.99 (m, 2H), 0.94 (d, 3H), 0.91 (d, 3H), 0.81 (d, 3H)
$^{13}$C NMR (75 MHz; CDCl$_3$) δ: 175.4, 150.5, 145.0, 113.4, 50.7, 44.3, 39.25, 34.3, 32.1, 28.7, 23.7, 22.1, 21.2, 16.1

EXAMPLE 2

Preparation of N-(2-pyridin-2-ylethyl)p-menthanecarboxamide [(1R,2S,5R)-2-isopropyl-5-methyl-N-(2-(pyridin-2-yl)ethyl)cyclohexanecarboxamide]

A preparation similar to that described in example 1 gives the desired product with the following spectroscopic properties:

MS: 288 ([M$^{+\bullet}$]), 273, 245, 149, 121, 95
$^1$H NMR (300 MHz; DMSO) δ: 8.53 (d, 1H), 7.62 (td, 1H), 7.16 (m, 2H), 6.43 (s, 1H), 3.67 (nontuplet, 2H), 3.00 (t, 2H), 1.95 (td, 1H), 1.84-1.53 (m, 4H), 1.47 (broad t, 1H), 1.4-1.1 (m, 2H), 0.87 (d, 3H), 0.84 (d,3H), 0.66 (d, 3H)
$^{13}$C NMR (75 MHz; DMSO) δ: 175.8, 159.7, 148.9, 136.7, 123.6, 121.55, 49.8, 44.3, 39.4, 38.35, 36.9, 34.6, 32.3, 28.55, 23.9, 22.3, 21.3, 15.95

EXAMPLE 3

Preparation of 2-isopropyl-2,3-dimethyl-N-(2-(pyridin-2-yl)ethyl)butanamide

A preparation similar to that described in example 1, using 2-isopropyl-2,3-dimethylbutanoyl chloride, gives the desired product with the following spectroscopic properties:
MS: 262 ([M+]), 220, 205, 149, 121, 106, 93
$^1$H NMR (300 MHz; CDCl3) 8.53 (d, 1H), 7.63 (t, 1H), 7.16 (m, 2H), 6.69 (s, 1H), 3.67 (dd, 2H), 2.99 (t, 2H), 1.96 (m, 2H), 0.96 (s, 3H), 0.85 (d, 6H), 0.79 (d, 6H) 13C (75 MHz; CDCL3) 175.6, 160.0, 149.1, 136.6, 123.4, 121.5, 51.4, 38.4, 36.9, 32.6, 18.1, 17.4, 14.1

EXAMPLE 4

Assessment of Cooling Effect

A small group of panelists is asked to taste various aqueous solutions of cooling compounds and indicate which solutions had a cooling intensity similar or slightly higher than that of a solution of menthol at 2 ppm. The same panel is asked to taste these solutions at the chosen concentrations and to record the cooling intensity at regular time intervals until no cooling could be sensed in the mouth. The results are shown in Table 2.

TABLE 2

Experiments on cooling intensity and longevity.

| Chemical | Concentration | Longevity |
|---|---|---|
| 1-Menthol | 2.0 ppm | 35 minutes |
| N-ethyl p-menthanecarboxamide (WS-3) | 1.5 ppm | 57 minutes |
| Formula I, m = 0, X = Y = Z = R1 = H, R2 + R3 = p-menthyl (compound of Example 1) | 0.5 ppm | 50 minutes |
| Formula I, m = 2, X = Y = Z = R1 = H, R2 + R3 = p-menthyl (compound of example 2) | 0.02 ppm | 60 minutes |
| Formula I, m = 2, X = Y = Z = H, R1 = methyl, R2 = R3 = isopropyl (compound of example 3) | 0.4 ppm | |

From Table 2, it can be seen that the compounds of Formula I are up to 100 times stronger and last longer than menthol, the reference cooling compound. Compounds of Formula I are also much stronger than WS-3, the best cooling compound of the prior art.

In a second experiment, the same panel is asked to taste various solutions of compounds having various concentrations and to indicate which of these solutions had a cooling intensity similar to or slightly higher than that of a solution of menthol at 2 ppm. This is the "isointensive concentration". The results are shown in Table 3.

TABLE 3

Intensity of compounds where $R^2 + R^3$ = p-menthane and $R^1 = X = Y = Z = H$

| Value of m (Chain length) | Position of main moiety on ring | Isointensive concentration |
|---|---|---|
| 0 | 2 or 6 | 0.2 ppm |
| 0 | 3 or 5 | 0.4 ppm |
| 0* | 4* | 0.5 ppm |
| 1 | 2 or 6 | 0.67 ppm |
| 1 | 3 or 5 | 0.25 ppm |
| 1 | 4 | 0.2 ppm |
| 2** | 2 or 6** | 0.02 ppm |
| 2 | 3 or 5 | 0.004 ppm |
| 2 | 4 | 0.05 ppm |

*compound of Example 1
**compound of Example 2

From Table 2 and 3, it can be seen that compounds of Formula I with various chain lengths and substitution patterns all have lower usage levels than the reference cooling chemicals, menthol and WS-3.

EXAMPLE 5

| Application in mouthwash | |
|---|---|
| Alcohol 95% | 177 mL |
| Sorbitol 70% | 250 g |
| Compound of example 1 as a 1% solution in alcohol | 50 mL |
| Peppermint oil, Terpeneless | 0.300 g |
| Methyl salicylate | 0.640 g |
| Eucalyptol | 0.922 g |
| Thymol | 0.639 g |
| Benzoic acid | 1.500 g |
| Pluronic ™ F127 nonionic surfactant | 5.000 g |
| Sodium Saccharin | 0.600 g |
| Sodium Citrate | 0.300 g |
| Citric Acid | 0.100 g |
| Water | q.s. 1 liter |

All the ingredients are mixed. 30 mL of obtained solution is put in the mouth, swished around, gargled and spit out. An icy-cool sensation is felt in every area of the mouth as well as lips.

EXAMPLE 6

| Application in toothpaste | |
|---|---|
| Opaque toothgel | 97.000 g |
| Compound of example 2 as a 2% solution in propylene glycol | 2.500 g |
| Peppermint oil, Terpeneless | 0.500 g |

The chemicals are mixed in the toothgel, a piece of toothgel is put on a toothbrush and a panelist's teeth are brushed. The mouth is rinsed with water and the water is spit out. An intense cooling sensation is felt by the panelist in all areas of the mouth.

EXAMPLE 7

Application in Beverages 1.5 mg of the compound of example 2 is dissolved in a 355 mL (12 fl oz.) can of clear lemon/lime soda. A panelist experiences an agreeable delayed cooling sensation in the mouth with no throat burning. No unpleasant after-taste is observed.

Although the invention has been described in detail through the above detailed description and the preceding examples, these examples are for the purpose of illustration only and it is understood that variations and modifications can be made by one skilled in the art without departing from the spirit and the scope of the invention. It should be understood that the embodiments described above are not only in the alternative, but can be combine.

The invention claimed is:

1. A method of providing a product with a cooling effect when applied to the mouth to give a cooling sensation, comprising the incorporation into the product of at least one compound of the formula I

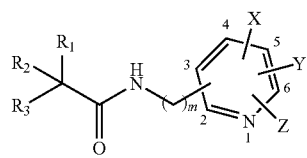

in which m is 2;
X, Y and Z are H;
$R^1$ is H and
$R^2$ and $R^3$ together form a 3-p-menthyl ring
wherein the at least one compound of formula I is isointensive to 2 ppm menthol at a concentration of 0.004 ppm to 0.05 ppm, and
wherein the product that is applied to the mouth is selected from the group consisting of foodstuffs, tobacco products, beverages, confectionaries, dentifrices, and mouthwashes.

2. The method according to claim 1, wherein the compound of formula I is used in combination with at least one other cooling compound comprising menthol, menthone, isopulegol, N-ethyl p-menthanecarboxamide, N,2,3-trimethyl-2-isopropylbutanamide, menthyl lactate, menthone glycerine acetal, mono-menthyl succinate, mono-menthyl glutarate, O-menthyl glycerine, menthyl-N,N-dimethylsuccinamate, or 2-sec-butylcyclohexanone.

3. The method according to claim 1, wherein the compound of the formula I comprises at least one of (1R,2S,5R)-2-isopropyl-5-methyl-N-(pyridinalkyl)cyclohexanecarboxamide or (2S,5R)-2-isopropyl-5-methyl-N-(pyridinalkyl)cyclohexanecarboxamide, wherein m =2.

4. The method according to claim 1, wherein the compound of the formula I comprises at least one of (1R,2S,5R)-2-isopropyl-5-methyl-N-(2-(pyridin-4-yl) ethyl)cyclohexanecarboxamide, (2S,5R)-2-isopropyl-5-methyl-N-(2-(pyridin-4-yl) ethyl)cyclohexanecarboxamide, or (1R,2S,5R)-2-isopropyl-5-methyl-N-(2-(pyridin-2-yl) ethyl) cyclohexanecarboxamide.

5. A method according to claim 1, wherein the position of the carboxamide group moiety on the ring is selected from the 3- and 5- positions.

6. A method according to claim 1, wherein the position of the carboxamide group moiety on the ring is selected from the 2- and 6- positions.

7. A method according to claim 1, wherein the position of the carboxamide group moiety on the ring is the 4- position.

8. The method according to claim 1, wherein the compound of the formula I comprises (1R,2S,5R)-2-isopropyl-5-methyl-N-(2-(pyridin-2-yl)ethyl) cyclo-hexane carboxamide.

9. The method of claim 1 wherein the product is applied by inhalation.

10. The method of claim 1 wherein the product is applied by oral ingestion.

11. A product that is applied to the mouth to give a cooling sensation, comprising at least one compound according to the formula I

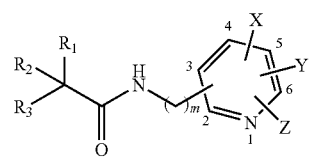

in which m is 2;
X, Y and Z are H;
$R^1$ is H and
$R^2$ and $R^3$ together form a 3-p-menthyl ring
wherein the at least one compound of formula I is isointensive to 2 ppm menthol at a concentration of 0.004 ppm to 0.05 ppm, and wherein the product that is applied to the mouth is selected from the group consisting of foodstuffs, tobacco products, beverages, confectionaries, dentifrices, and mouthwashes.

12. The product according to claim 11, wherein the product is used in combination with at least one other cooling compound comprising menthol, menthone, isopulegol, N-ethyl p-menthanecarboxamide, N,2,3-trimethyl-2-isopropylbutanamide, menthyl lactate, menthone glycerine acetal, mono-menthyl succinate, mono-menthyl glutarate, O-menthyl glycerine, menthyl-N,N-dimethylsuccinamate, or 2-sec-butylcyclohexanone.

13. The product according to claim 11, wherein the compound of the formula I comprises at least one of (1R,2S,5R)-2-isopropyl-5-methyl-N-(pyridinalkyl)cyclohexanecarboxamide or (2S,5R)-2-isopropyl-5-methyl-N-(pyridinalkyl)cyclohexanecarboxamide, wherein m =2.

14. The product according to claim 11, wherein the compound of the formula I comprises at least one of (1R,2S,5R)-2-isopropyl-5-methyl-N-(2-(pyridin-4-yl) ethyl)cyclohexanecarboxamide, (2S,5R)-2-isopropyl-5-methyl-N-(2-(pyridin-4-yl) ethyl)cyclohexanecarboxamide, or (1R,2S,5R)-2-isopropyl-5-methyl-N-(2-(pyridin-2-yl) ethyl)cyclohexanecarboxamide.

15. The product according to claim 11, wherein the position of the carboxamide group moiety on the ring is selected from the 3- and 5- positions.

16. The product according to claim 11, wherein the position of the carboxamide group moiety on the ring is selected from the 2- and 6- positions.

17. The product according to claim 11, wherein the position of the carboxamide group moiety on the ring is the 4- position.

18. The product according to claim 11, wherein the compound of the formula I comprises (1R,2S,5R)-2-isopropyl-5-methyl-N-(2-(pyridin-2-yl)ethyl)cyclo-hexane carboxamide.

19. The product of claim 11 wherein the product is applied by inhalation.

20. The product of claim 11 wherein the product is applied by oral ingestion.

21. A product selected from the group consisting of foodstuff, tobacco product, beverage, confectionary, dentifrice, and mouthwash, comprising an amount of a compound of formula I,

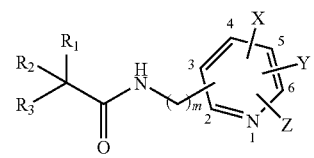

in which m is 2;
X, Y and Z are H;
$R^1$ is H and
$R^2$ and $R^3$ together form a 3-p-menthyl ring
wherein the at least one compound of formula I is isointensive to 2 ppm menthol at a concentration of 0.004 ppm to 0.05 ppm, and wherein the amount of the compound is effective to give a cooling sensation to the mouth.

22. The product according to claim 21, wherein the compound of the formula I comprises at least one of (1R,2S,5R)-2-isopropyl-5-methyl-N-(pyridinalkyl) cyclohexanecarboxamide or (2S,5R)-2-isopropyl-5-methyl-N-(pyridinalkyl) cyclohexanecarboxamide, wherein m =2.

23. The product according to claim 21, wherein the compound of the formula I comprises at least one of (1R,2S,5R)-2-isopropyl-5-methyl-N-(2-(pyridin-4-yl) ethyl)cyclohexane carboxamide, (2S,5R)-2-isopropyl-5-methyl-N-(2-(pyridin-4-yl)ethyl) cyclohexane carboxamide, or (1R,2S,5R)-2-isopropyl-5-methyl-N-(2-(pyridin-2-yl) ethyl) cyclohexane carboxamide.

24. The product according to claim 21, wherein the compound of the formula I comprises (1R,2S,5R)-2-isopropyl-5-methyl-N-(2-(pyridin-2-yl)ethyl)cyclo-hexane carboxamide.

* * * * *